US005496955A

United States Patent [19]
Becker et al.

[11] Patent Number: 5,496,955
[45] Date of Patent: Mar. 5, 1996

[54] PREPARATION OF D-HISTIDINE AND DERIVATIVES THEREOF FROM L-HISTIDINE

[75] Inventors: Yigal Becker; Yonit Assaf-Biran, both of Tel Aviv; Youval Shvo, Kfar Shmariahu, all of Israel

[73] Assignee: Bromine Compounds Limited, Beer-Sheva, Israel

[21] Appl. No.: 122,805

[22] Filed: Sep. 16, 1993

Related U.S. Application Data

[63] Continuation of Ser. No. 728,893, Jul. 10, 1991, abandoned.

[30] Foreign Application Priority Data

Jul. 11, 1990 [IL] Israel ............................................ 95038

[51] Int. Cl.$^6$ .................................................. C07D 233/64
[52] U.S. Cl. ........................................ 548/334.5; 548/339.1
[58] Field of Search ................................ 548/334.5, 339.1

[56] References Cited

U.S. PATENT DOCUMENTS

| | | | |
|---|---|---|---|
| 4,401,820 | 8/1983 | Chibata et al. | 548/344 |
| 4,612,324 | 9/1986 | Cashin et al. | 548/344 |

OTHER PUBLICATIONS

Yamada, et al. *J. Org. Chem.*, vol. 48, pp. 843–846, 1983.
Shiraiwa, et al., *Chemistry Letters*, pp. 2041–2042, 1987.
Yamada et al, Agric. Biol. Chem., vol. 41(12), pp. 2413–2416 (1977).

*Primary Examiner*—Floyd D. Higel
*Attorney, Agent, or Firm*—Michael N. Meller

[57] ABSTRACT

D-histidine and its derivatives are manufactured from L-histidine, by mixing L-histidine and tartaric acid with an aldehyde in acetic acid medium and thereafter precipitating D-histidine tartrate from the reaction mass. Pure D-histidine can then be recovered from the crude D-histidine tartrate.

15 Claims, No Drawings

PREPARATION OF D-HISTIDINE AND DERIVATIVES THEREOF FROM L-HISTIDINE

This application is a continuation of application Ser. No. 728,893, filed Jul. 10, 1991, now abandoned.

FIELD OF THE INVENTION

The present invention relates to the preparation of D-histidine and derivatives thereof, in particular D-histidine methyl ester dihydrochloride, from L-histidine, specifically by asymmetric transformation of L-histidine.

BACKGROUND OF THE INVENTION

D-histidine is a more desirable industrial product than L-histidine and therefore the transformation of L-histidine to D-histidine is highly desirable. Such transformation, however, has never been carried out, to the applicant's knowledge.

THE PRIOR ART

The optical resolution of racemic mixtures of D-histidine and L-histidine by diastereomeric separation has been known for some time. F. L. Pyman, J. Chem. Soc., 99, 1386 (1911) teaches that an aqueous solution containing a racemic mixture of D- and L-histidine and tartaric acid selectively gives the less-soluble salt composed of equimolar amounts of D-histidine and tartaric acid. It has recently been reported by S. Yamada et al., J. Org. Chem., 48, 843 (1983) that free amino adds are racemized in the presence of aldehydes in acetic acid. An asymmetric transformation of D, L-4-thiazolidine carboxylic acid has been achieved in acetic acid using salicylic aldehyde and tartaric acid as resolving agent, as reported by T. Shitaiwa et al., Chem. Lett., 2041 (1987).

SUMMARY OF THE INVENTION

The present invention provides an asymmetric transformation of L-histidine into D-histidine. According to the invention, L-histidine and tartaric acid are mixed with optionally substituted salicylic aldehyde in acetic acid medium, whereby the soluble L-histidine tartrate salt is formed and racemized, and thereafter D-histidine tartrate (bitartrate) is precipitated from the reaction mass. Pure D-histidine is then recovered from the crude D-histidine tartrate. Derivatives of D-histidine such as esters, can also be prepared according to the invention, in particular D-histidine methylester dihydrochloride (D-his OCH$_3$.2HCl).

The molar ratio of salicylic aldehyde to starting L-histidine may be comprised between 0.01 and 2, and preferably between 0.1 and 1.0. The most preferred molar ratio is 0.5 salicylic aldehyde to D-histidine. Decreasing or increasing said ratio tends to give a less pure product.

The reaction of L-histidine and tartaric acid with salicylic aldehyde in acetic acid medium is preferably carried out at temperatures from 80° C. to reflux temperature. At lower temperatures, such as 50°–60° C., the reaction is slower and incomplete.

Precipitation of the crude D-histidine tartrate is carried out at temperatures from 60°–110° C., and preferably from 80°–95° C.

The concentration of the starting L-histidine in the acetic acid may vary from 5% w/v and 20% w/v, but is preferably contained between the limits of 7.5% w/v to 16% w/v. Departure from the preferred limits results in a decrease of purity, but this may not be such as to render the process practically inoperative. Furthermore, it was found that the filtrate of acetic acid and salicylic aldehyde recovered 90% after filtration of the crude D-His-TA can be reused several times (5–6 times) with no significant change in the quality of the D-His-TA.

The reaction of L-histidine and tartaric acid with the salicylic aldehyde, at the aforesaid temperatures, may preferably vary from 1 to 3 hours. If heating is prolonged, a darker and less pure product may be obtained, and if this disadvantage is tolerable, heating times up to 5 hours may be acceptable.

The reaction medium should preferably be anhydrous. The presence of water is undesirable in that it slows down the reaction and decreases the yield by dissolving the final product. The following table demonstrates the effect of water.

| % H$_2$O in HOAC | Beginning of precipitation (min.) | Yield (%) |
|---|---|---|
| 0 | 5 | 93–96 |
| 10 | 7 | 93 |
| 20 | 17 | 50 |
| 50 | — | — |

Pure D-histidine is recovered from the crude D-histidine bitartrate obtained from the reaction of L-histidine with salicylic aldehyde and subsequent precipitation. The crude salt first undergoes a partial purification, which removes the more soluble L-His-(+)TA present in the crude D-His-(+)TA in amounts of 15–20% w/v, by stirring with water at temperatures from 60° to 100°, and preferably from 75° to 85°, and subsequent cooling below 50° C. and filtration. The semi-crude salt thus obtained is first treated with sodium hydroxide, whereby the D-histidine tartrate is decomposed, and subsequently with calcium chloride, whereby the tartaric anion is quantitatively removed from the solution as calcium tartrate, which is precipitated. Equivalent amounts of NaOH and CaCl$_2$ are preferably used, and in any case, large excesses of NaOH are avoided. The calcium tartrate thus obtained is filtered and washed with water. From the filtrate D-histidine is obtained by acidification to the isoelectric point (pH=7.50).

DETAILED DESCRIPTION OF PREFERRED EMBODIMENTS

The invention will be illustrated by the following examples.

EXAMPLE 1

Preparation of crude D-histidine tartrate from L-histidine

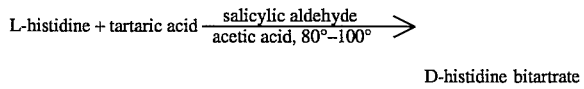

D-histidine bitartrate

The following reagents were employed in the following amounts:

| L-histidine | 15.5 g | 0.1 mole | |
| tartaric acid (TA) | 15.1 g | 0.1 mole | |
| salicylic aldehyde | 6.1 g | 5.20 ml | 0.05 mole |

| acetic acid | 190 ml |

A mixture of 0.1 mole (15.5 g) of L-histidine, 0.1 mole (15.1 g) of (+)TA and 0.05 mole (5.2 ml) of salicylic aldehyde in 190 ml (~6 volumes, per volume of crude D-His-TA) of acetic acid was stirred mechanically for 1.5 hr at 80°–100° C. The mixture was cooled to 15° C.; the formed salt was filtered. Crude D-histidine bitartrate was obtained in 96% yield. Analysis indicates that it contains 80–83% pure D-histidine bitartrate.

EXAMPLE 2

Preparation of pure D-histidine from the crude D-histidine bitartrate

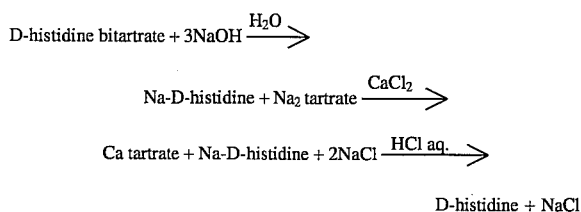

D-histidine + NaCl

The following reagents were employed in the following amounts:

| | |
|---|---|
| crude D-histidine bitartrate from Example 1 | 10 g |
| H$_2$O (for stirring) | 15 ml (1.5 volumes) |
| H$_2$O (as reaction medium) | 15 ml |
| sodium hydroxide (fine pellets) | 3.6 g 0.09 mole |
| calcium chloride | 3.33 g 0.03 mole |
| hydrochloric acid 32% | 3 ml |
| H$_2$O (for washing) | 5 ml |
| methanol (for washing) | 6 ml |

10.0 g of the crude salt from Example 1 were stirred in 15 ml H$_2$O at 80°–90° C. for 30 minutes, cooled below 50° C. and filtered. The solid salt containing 0.03 mole D-histidine tartrate ([α]$_D$+12.17° –C=1.61,H$_2$O) was suspended in 15 ml H$_2$O. With stirring, 0.09 mole (3.6 g) of sodium hydroxide was added and a clear solution was formed. Heat was evolved. Calcium chloride, 0.03 mole (3.33 g) was added and the mixture was stirred at 10°–15° C. for one hour to enable complete precipitation of calcium tartrate. The solid was filtered and washed thoroughly with 3 ml H$_2$O. The filtrate was neutralized with hydrochloric acid 32% (3 ml) to pH=7.5 (isoelectric point) and cooled to 0°–10° C. with stirring for one hour to deposit the free amino acid. The white solid was collected by filtration, washed twice with 3 ml cold methanol: H$_2$O 2:1, then with 2 ml methanol, and dried in vacuo (100° C.) for two hours. D-histidine was obtained in 71.2% yield (3.31 g) with optical purity of 99% ([α]=+39.33). Overall yield from L-histidine=64%. Assay (potentiometric titration, 0.1 NHCl) is 98.99%.

The amount of water used in the aforesaid example as reaction medium is the optimal amount. Smaller amounts will cause co-precipitation of sodium chloride with the product, while larger amounts will dissolve the product and lower the yield. Smaller variations from the optimal value are however admissible if the resulting disadvantages are tolerable. Some (17–20%) of the theoretical amount of the total D-histidine remains in the mother liquor. This quantity was determined by measuring the rotation of the mother liquor and the concentration of D-histidine was calculated using its specific rotation. The total D-histidine obtained from L-histidine is therefore 80–83%. The rest is unchanged L-histidine which was removed in the purification of the crude D-His-TA by water treatment.

EXAMPLE 3

Preparation of D-histidine methyl ester dihydrochloride from crude D-histidine bitartrate

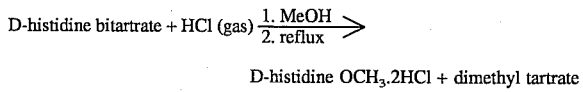

D-histidine OCH$_3$.2HCl + dimethyl tartrate

The following reagents were used in the following amounts:

| | |
|---|---|
| crude D-histidine bitartrate from Example 1 | 8.0 g |
| H$_2$O (for stirring) | 24 ml (3 volumes) |
| methanol (for stirring) | 32 ml (4 volumes) |
| methanol (for reaction) | 120 ml |
| hydrogen chloride (gas) | — |
| methanol (crystallization & washings) | 15 ml |
| t-butylmethylether (TBME) (crystallization & washings) | 45 ml |

8.0 g of the crude salt from Example 1 were stirred in 24 ml of H$_2$O at 80°–90° C. for 30 minutes, cooled below 50° C. and filtered. The solid was stirred with 32 ml methanol for one hour at 15°–25° C. The filtered precipitate was suspended in 60 ml methanol. Dry HCl was introduced into the stirred suspension without cooling for 20 minutes (weak reflux was observed). Another 60 ml methanol were added and the mixture was refluxed for 1.5 hours. Most of the solvent was distilled out, forming a syrup or wet solid. Methanol (10 ml) was added followed by 30 ml of TBME. The mixture was stirred for one hour at 15°–20° C., then cooled to 5° C. and filtered. The white solid was washed three times with a mixture of 5 ml methanol:TBME (1:2). The ester dihydrochloride salt was dried in vacuo for 1.5 hours at 60°–75° C. and was obtained in 94.5% yield (4.573 g), based on tartrate after methanol purification. ([α]=–9.16 ([α]) Lit –9.0).

Stirring with methanol in the process hereinbefore described is necessary for the subsequent acidification. It removes traces of salicylic aldehyde which otherwise would cause racemization during esterification. Mere washing with methanol is not sufficient.

EXAMPLE 4

Preparation of crude D-histidine tartrate from L-histidine

The operations carried out in this example are the same as those of Example 1, but a smaller amount of acetic acid has been used. The amounts of the reagents were:

| | | |
|---|---|---|
| L-His | 15.5 g | 0.1 mole |
| L-(+)-TA | 15.1 g | 0.1 mole | salicylaldehyde 6.1 g, 5.2 ml, 0.05 mole
acetic acid 95 ml

A mixture of 0.1 mole (15.5 g) of L-histidine, 0.1 mole (15.1 g) of (+) tartaric acid and 0.05 mole (5.2 ml) of salicylaldehyde in 95 ml of acetic acid was stirred mechanically for two hours at 80°–100° C. The mixture was cooled to 25° C. and the formed salt was filtered. The crude D-histidine bitartrate (a very light yellow solid) was obtained in 97% yield. The volume of recovered acetic acid containing salicylaldehyde was 85 ml (89.5% recovery). The crude D-His-(+)TA was stirred and heated in 45 ml water at 80°–90° C. for 35 minutes, cooled to 30° C. and filtered. Drying in air gave 26.7 g (87.5%) of pure D-His-(+)TA. $[\alpha]^{18}_D = +13.04 [C=1.35, H_2O]$.

EXAMPLE 5

Recycling of the acetic acid-salicylaldehyde from Example 4,

To a mixture consisting of 15.5 g L-histidine, 15.1 g L-(+)-tartaric acid was added 85 ml of the recovered acetic acid solution containing salicylaldehyde from the previous experiment. Additional 10 ml acetic acid containing 0.54 ml salicylaldehyde was added, and the mixture was stirred and heated as above at 80°–100° C. for two hours. After cooling to 25° C. the crude product D-His-(+)TA was filtered. 79 ml of acetic acid containing salicylaldehyde was recovered (83.2%). After stirring in hot water as above, pure D-His-(+)TA was obtained, 25.9 g (85% yield from L-His).

This procedure was repeated an additional three times without any noticeable change in results.

EXAMPLE 6

Recovery of L-His-(+)TA from crude D-His-(+)TA.

Example 4 was repeated, the crude D-His-(+)TA was filtered at 100° C. The recovered acetic acid solution containing salicylaldehyde was obtained in 91.3% recovery. The crude D-His-(+)TA was slurried in MeOH (60 ml) at room temperature for 30 minutes, then filtered and air-dried to afford 30.01 g of crude, salicylaldehyde-free D-His-(+)TA. The crude salt was heated in 60 ml water at 80°–90° C. for 30 minutes, cooled to 40° C. and filtered. The pure D-His-(+)TA amounted to 23.83 g (78.13%). The aqueous filtrate was evaporated to dryness to afford 6.5 g of L-His-(+) TA $[\alpha]_D^{27} +12.53 (C=1.9, H_2O)$ which can be reused for subsequent transformations. Total recovery of diastereomeric tartrates was ≧99%.

EXAMPLE 7

Use of 3,5-dichlorosalicylaldehyde

Example 4 was repeated, except 3,5-dichlorosalicylaldehyde (9.55 g, 0.05 mole) was used instead of salicylaldehyde. The crude D-His-TA had an intense yellow color. It was freed from the aldehyde by stirring at room temperature in 60 ml acetone for one hour. The yellow solid obtained after filtration was stirred and heated in 90 ml water at 83° C. for 45 minutes.

There was obtained 23.4 g of purified D-His-(+)TA. Conversion of the crude or purified D-His-(+)TA to D-histidine gave 66.8% D-histidine, $[\alpha]_D = +29.23°$ (C=1.04, $H_2O$), 74.3% optically pure.

When Example 4 was repeated using 1.91 g, 0.01 mole of 3,5-dichlorosalicylaldehyde, D-histidine was obtained in 66.35% from the purified D-His-(+)TA, $[\alpha]_D=+26.6°$ (C=1.03, $H_2O$) or 67.63% optically pure.

EXAMPLE 8

Direct conversion of D-His-(+)TA to D-histidine methylester dihydrochloride.

The purified D-His-(+)TA from Example 4 was freed from traces of salicylaldehyde by stirring in 90 ml methanol for one hour. Purified D-His-(+)TA, 24.29 g was then suspended in methanol (180 ml, 7.4 volumes) and HCl gas was passed through the stirred suspension. After 5 minutes, all the solid dissolved. Heat was evolved. More HCl gas was passed for an additional 10 minutes. Some precipitate was formed. The mixture was heated to reflux for 1.5 hours. TLC analysis on silica plates (EtOH: 25% aqueous $NH_3$=8:2) indicated that traces of D-histidine were present. Work-up in the usual way gave 17.36 g (90% yield) of colorless crystals. $[\alpha]_D=-9.85°$ (C=2.01, $H_2O$).

A number of illustrative embodiments of the invention have been described. The invention may of course be carried out with a number of modifications and adaptations, within the abilities of a person skilled in the art, without departing from the spirit of the invention, and from the appended claims.

We claim:

1. A process for manufacture of D-histidine or esters thereof from L-histidine, comprising the steps of mixing L-histidine and tartaric acid with an aldehyde selected from the group consisting of salicylaldehyde and 3,5-dichlorosalicylaldehyde in an acetic acid medium and thereafter precipitating D-histidine tartrate from the reaction mass.

2. A process according to claim 1, further comprising recovering pure D-histidine from the crude D-histidine tartrate.

3. A process according to claim 1, wherein the molar ratio of the salicylic aldehyde to starting L-histidine is in the range of 0.01 and 2.

4. A process according to claim 1 wherein the reaction of L-histidine and tartaric acid with the aldehyde in the acetic acid medium is carried out at temperatures from 80° C. to reflux temperature.

5. A process according to claim 1, wherein the precipitation of the crude D-histidine tartrate is carried out at temperatures from 60° to 100° C.

6. A process according to claim 1, wherein the concentration of the starting L-histidine in the acetic acid is between 5% w/v and 20% w/v.

7. A process according to claim 1, wherein the medium of the reaction between L-histidine and tartaric acid with the aldehyde is essentially anhydrous.

8. A process according to claim 1, further comprising the step of reacting the crude D-histidine tartrate with hydrochloric acid and methanol at reflux temperature to produce D-histidine methylester dihydrochloride.

9. A process according to claim 2, wherein the crude D-histidine tartrate is partially purified by stirring with water, and is then decomposed by treating it with NaOH, the resulting solution is treated with calcium chloride to precipitate calcium tartrate, and is then acidified with hydrochloric acid to the isoelectric point.

10. A process according to claim 2, wherein the molar ratio of the salicylaldehyde to starting L-histidine is in the range of 0.01 and 2.

11. A process according to claim 10, wherein the molar ratio between the salicylic aldehyde and starting L-histidine is about 0.5.

12. A process according to claim 3, wherein the molar ratio of salicylicaldehyde to starting L-histidine is in the range of 0.1 to 1.0.

13. A process according to claim 5, wherein the temperature range is between 80° and 95° C.

14. A process according to claim 6, wherein the concentration of the starting L-histidine in the acetic acid is between 7.5% w/v and 16% w/v.

15. A process according to claim 1, wherein the reaction between L-histidine and the aldehyde is carried out in from 1 to 3 hours.

* * * * *